United States Patent [19]

Kobzina

[11] 4,097,265
[45] Jun. 27, 1978

[54] 3,5-DIMETHYL-2-THIENYLCARBOXANILIDE AND 3,5-DIMETHYL-2-THIENYL-(N-HALOALKYLTHIOCARBOXANILIDE) HERBICIDES

[75] Inventor: John W. Kobzina, Walnut Creek, Calif.

[73] Assignee: Chevron Research Company, San Francisco, Calif.

[21] Appl. No.: 764,125

[22] Filed: Jan. 31, 1977

Related U.S. Application Data

[60] Division of Ser. No. 645,159, Dec. 30, 1975, abandoned, which is a continuation of Ser. No. 570,339, May 21, 1975, Pat. No. 3,948,633, which is a division of Ser. No. 383,751, Jul. 30, 1973, Pat. No. 3,892,775.

[51] Int. Cl.² .................... A01N 9/12; C07D 63/16
[52] U.S. Cl. .................................. 71/90; 260/332.2 C
[58] Field of Search ................. 71/90; 260/332.2 C

[56] References Cited

U.S. PATENT DOCUMENTS

| 3,158,624 | 11/1964 | Leon et al. | 260/347.3 |
| 3,303,201 | 2/1967 | Stecker | 260/332.2 |
| 3,536,473 | 10/1970 | Popoff et al. | 71/90 |

FOREIGN PATENT DOCUMENTS

| 2,011,214 | 2/1970 | France | 260/347.3 |

*Primary Examiner*—Catherine L Mills
*Attorney, Agent, or Firm*—Dix A. Newell; T. G. DeJonghe; Raymond Owyang

[57] ABSTRACT

Novel 3,5-dimethyl-2-thienylcarboxanilides and 3,5-dimethyl-2-thienyl-(N-haloalkylthiocarboxanilides) are active pre- and post-emergent herbicides.

9 Claims, No Drawings

3,5-DIMETHYL-2-THIENYLCARBOXANILIDE AND 3,5-DIMETHYL-2-THIENYL-(N-HALOALKYLTHI- OCARBOXANILIDE) HERBICIDES

This is a division of application Ser. No. 645,159, filed Dec. 30, 1975 now abandoned, which in turn is a continuation of application Ser. No. 570,339, filed May 21, 1975, now U.S. Pat. No. 3,948,633, which in turn is a division of application Ser. No. 383,751, filed July 30, 1973, now U.S. Pat. No. 3,892,775.

DESCRIPTION OF THE PRIOR ART

British Pat. No. 1,215,066, published Dec. 9, 1970, discloses fungicidal 2-thienylcarboxanilides, such as 3-methyl-2-thienylcarboxanilide.

French Pat. No. 1,563,735, published Apr. 18, 1969, discloses herbicidal, nematocidal and fungicidal trichloro-2-thienylcarboxanilides, such as 3,4,5-trichloro-2-thienylcarboxanilide.

*Chemical Abstracts*, 72, 31613t (1970); 73, 98779r (1970); 73, 98933m (1970); 73, 108740n (1970); and 76, 46068a (1972), disclose pesticidal furylcarboxanilides and furylcarboxamides.

DESCRIPTION OF THE INVENTION

The thienylcarboxanilides of the invention may be represented by the following formula (I):

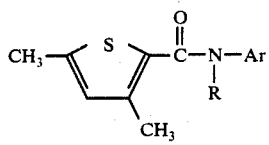

wherein R is hydrogen, lower alkyl or polyhaloalkylthio of 1 to 2 carbon atoms and 3 to 5 chloro or bromo groups and Ar is phenyl or 2-fluorophenyl.

Representative lower alkyl groups are methyl, ethyl, n-propyl, isopropyl and butyl. Representative polyhaloalkylthio groups are trichloromethylthio, bromodichloromethylthio, 1,1,2,2-tetrachloroethylthio, 1,2,2,2-tetrachloroethylthio and pentabromoethylthio.

The preferred R group is hydrogen or polyhaloalkylthio. Particularly preferred polyhaloalkylthio R groups are polychloroalkylthio, especially trichloromethyl and tetrachloroethyl.

The preferred Ar group is phenyl.

Illustrative compounds of Formula I are:

3,5-dimethyl-2-thienylcarboxanilide
3,5-dimethyl-2-thienyl-(N-methylcarboxanilide)
3,5-dimethyl-2-thienyl-(N-propylcarboxanilide)
3,5-dimethyl-2-thienyl-(N-trichloromethylthiocarboxanilide)
3,5-dimethyl-2-thienyl-(N-1,1,2,2-tetrachloroethylthiocarboxanilide)
3,5-dimethyl-2-thienyl-(N-2-fluorophenylcarboxamide)
3,5-dimethyl-2-thienyl-(N-2-fluorophenyl-N-methylcarboxamide)
3,5-dimethyl-2-thienyl-(N-2-fluorophenyl-N-trichloromethylthiocarboxamide) and
3,5-dimethyl-2-thienyl-(N-2-fluorophenyl-N-1,1,2,2-tetrachloroethylthiocarboxamide.

The compounds of the invention wherein R is hydrogen or lower alkyl are prepared by reacting methyl 3,5-dimethyl-2-thiophenecarboxylate with a magnesium iodide derivative of aniline or 2-fluoroaniline, as depicted in the following equation (1):

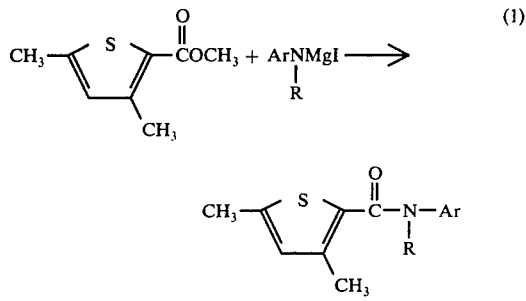

wherein R is hydrogen or lower alkyl and Ar has the same significance as previously defined.

The reaction depicted by equation (1) is conducted by reacting substantially equimolar amounts of the methyl 3,5-dimethyl-2-thiophenecarboxylate and the magnesium iodide derivative of aniline or 2-fluoroaniline in an inert solvent at a temperature of 0° to 50° C. If desired, one to two molar excess of the magnesium iodide derivative may be employed. The product is isolated and purified by conventional procedures such as filtration, extraction, chromatography, etc.

The methyl 3,5-dimethyl-2-thiophenecarboxylate reactant is a known compound and is prepared as described in German Pat. No. 1,088,507 [Chem. Abst. 56, 456 (1962)]. The magnesium iodide derivative of aniline or 2-fluoroaniline is prepared by reacting aniline or 2-fluoroaniline with methyl magnesium iodide.

The compounds of the invention wherein R is polyhaloalkylthio are prepared by sulfenylating a 3,5-dimethyl-2-thienylcarboxanilide, as depicted in the following equation (2):

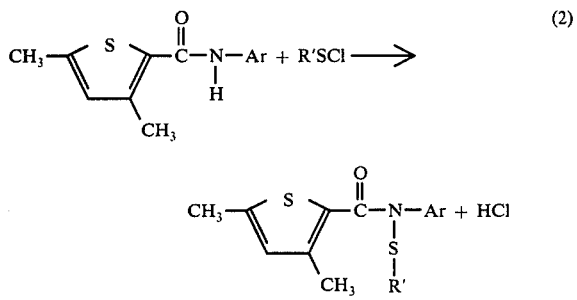

wherein Ar has the same significance as previously defined and R' is polyhaloalkyl of 1 to 2 carbon atoms and 3 to 5 chloro or bromo groups, e.g., trichloromethyl, 1,1,2,2-tetrachloroethyl, etc.

The reaction depicted in equation 2 is conducted by reacting substantially equimolar amounts of the carboxanilide and the sulfenyl chloride in the presence of a basic acceptor. Suitable basic acceptors are organic amines such as pyridine compounds and trialkylamines. Generally, at least one mol of basic acceptor is employed for each mol of sulfenyl chloride. The reaction is normally conducted in a polar organic solvent, such as dimethylformamide, acetonitrile or dimethoxyethane, at a temperature of 0° to 50° C. The product is isolated and purified by conventional procedures such as extraction, filtration, crystallization and chromatography.

The preparation of the compounds of the invention is illustrated by the following examples.

EXAMPLES

EXAMPLE 1

Preparation of 3,5-dimethyl-2-thienylcarboxanilide

A sample of 14.2 g (0.1 mol) methyl iodide was added dropwise to 2.43 g (0.1 mol) magnesium turnings in 30 ml diethyl ether. A solution of 9.31 g (0.1 mol) aniline in 30 ml diethyl ether was then added dropwise to the resulting solution of methyl magnesium iodide. After the reaction mixture was stirred for 15 minutes, 8.51 g (0.05 mol) methyl 3,5-dimethylthiophene-2-carboxylate and about 100 ml diethyl ether were added to the reaction mixture. The reaction mixture was stirred at reflux for 2 hours and then allowed to stand at about 25° C. overnight. 50 ml of water and a small amount of hydrochloric acid solution were added to the reaction mixture to dissolve the magnesium salts. The ether phase was separated, dried over magnesium sulfate and sodium carbonate and evaporated under reduced pressure to give an oil. Unreacted aniline was removed from the oil by distillation at 100° C. and 0.1 mm of Hg. The oil was then chromatographed on silica gel. Elution with 10% ether/90% hexane gave unreacted methyl 3,5-dimethylthiophene-2-carboxylate. Elution with 100% ether gave the 3,5-dimethyl-2-thienylcarboxanilide product, as a white, fluffy solid, m.p. 98°–101° C. Elemental analysis for $C_{13}H_{13}NOS$ showed: %S, calculated 13.86; found 13.77.

EXAMPLE 2

Preparation of 3,5-dimethyl-2-thienyl-(N-trichlormethylthiocarboxamide)

A 4.4-g sample of trichloromethylsulfenyl chloride was added to a solution of 5.0 g 3,5-dimethyl-2-thienyl-(N-trichloromethylthiocarboxamide) in 50 ml dimethoxyethane. A 2.2-g sample of triethylamine was then added dropwise to the solution at 0° C. The reaction mixture was stirred at 0° C. for 1 hour and then at about 25° C. for ½ hour. The reaction mixture was filtered and the filtrate was evaporated to give an oil. The oil was chromatographed on silica gel (10% ether/90% hexane eluants) to give the product as a tan solid, m.p. 82°–82.5° C. Elemental analysis for $C_{14}H_{12}Cl_3NOS_2$ showed: %S, calculated 16.48; found 16.1; %Cl calculated 27.93; found 28.9.

EXAMPLE 3

Preparation of 3,5-dimethyl-2-thienyl-(N-2-fluorophenylcarboxamide)

A solution of methyl magnesium iodide was prepared by the dropwise addition of 19.97 g methyl iodide to 3.6 g magnesium turnings in 100 ml diethyl ether. To the solution of methyl magnesium iodide was then added dropwise 12 g 2-fluoroaniline at ambient temperature. The reaction was exothermic. A solution of 12 g methyl 3,5-dimethylthiophene-2-carboxylate in 20 ml diethyl ether was then added. The reaction mixture was heated in a bath maintained at 55° C. for 2 hours and then allowed to stand overnight at about 25° C. 50 ml water and a small amount of hydrochloric acid solution were added to the reaction mixture to dissolve the magnesium salts produced in the reaction. The organic layer was separated, dried over a mixture of magnesium sulfate and sodium carbonate and evaporated under reduced pressure. The residue was chromatographed on silica gel (10% ether/90% hexane eluant) to give the product as a white solid, m.p. 73°–74° C. Elemental analysis for $C_{13}H_{12}FNOS$ showed: %S calculated 12.86, found 12.88; %F calculated 7.62, found 7.58.

UTILITY

The compounds of the present invention are, in general, herbicidal in both pre- and post-emergent applications. For pre-emergent control of undesirable vegetation, the herbicidal compounds will be applied in herbicidally effective amounts to the environment or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaf weeds. Some may be selective with respect to the type of application and/or type of weed.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour, or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally, for both pre- and post-emergent control, the herbicidal compounds of the invention are applied at rates of 0.2 to 60 kg/ha., and the preferred rate is in the range 0.5 to 40 kg/ha.

Pre- and post-emergent herbicidal tests on representative compounds of the invention were made using the following methods:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 μ/cm². The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill.

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 33 μ/cm². After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill.

The results (average of 3 tests) of these tests appear in Table I. For comparison, a variety of closely related thienyl carboxanilides and carboxamides were also tested.

In Table I, the following abbreviations are employed:

O = Wild Oats (*Avena fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

TABLE I

| Compound | Herbicidal Effectiveness Pre-Emergent/Post-Emergent | | | | | |
|---|---|---|---|---|---|---|
|  | O | W | C | M | P | L |
| 3,5-dimethyl-2-thienylcarboxanilide | 95/0 | 100/0 | 100/0 | 95/60 | 100/40 | 95/60 |
| 3,5-dimethyl-2-thienyl-(N-trichloromethylthiocarboxanilide | 0/30 | 0/65 | 0/20 | 100/85 | 95/50 | 100/100 |
| 3,5-dimethyl-2-thienyl-(N-2-fluorophenylcarboxamide) | 93/40 | 100/40 | 100/0 | 100/60 | 100/20 | 100/65 |
| 3-methyl-2-thienylcarboxanilide | 0/0 | 0/0 | 0/0 | 0/0 | 0/0 | 0/0 |
| 3-methyl-2-thienyl-(N-2-fluorophenylcarboxamide) | 0/0 | 0/0 | 0/0 | 10/0 | 0/0 | 15/0 |
| 4-methyl-2-thienylcarboxanilide | 0/0 | 0/0 | 0/0 | 15/0 | 0/0 | 0/0 |
| 4-methyl-2-thienyl-(N-3-tolylcarboxamide) | 0/0 | 0/0 | 0/0 | 0/0 | 0/0 | 0/0 |
| 4-methyl-2-thienyl-(N-2-fluorophenylcarboxamide) | 0/20 | 0/20 | 0/10 | 0/35 | 0/20 | 0/25 |
| 4-methyl-5-chloro-2-thienyl-(N-2-fluorophenylcarboxamide) | 0/0 | 0/0 | 0/10 | 0/25 | 0/25 | 0/25 |
| 4-methyl-5-chloro-2-thienyl-(N-4-chlorophenylcarboxamide) | 0/0 | 0/0 | 0/0 | 0/0 | 0/0 | 0/0 |
| 4-methyl-5-chloro-2-thienylcarboxanilide | 0/0 | 0/0 | 0/0 | 0/0 | 0/0 | 0/0 |
| 4-methyl-5-chloro-2-thienyl-(N-3-tolylcarboxamide) | 0/0 | 0/0 | 0/0 | 0/0 | 0/0 | 0/0 |
| 3,4-dimethyl-2-thienylcarboxanilide | 0/0 | 0/0 | 0/0 | 0/0 | 0/0 | 0/0 |
| 3,4-dimethyl-2-thienyl-(N-2-fluorophenylcarboxamide) | 0/0 | 0/0 | 0/0 | 0/0 | 0/0 | 0/0 |
| 2,5-dimethyl-3-thienylcarboxanilide | 0/0 | 0/0 | 0/0 | 0/0 | 0/0 | 0/0 |
| 3,5-dimethyl-2-thienyl-(N-4-chlorophenylcarboxamide) | 0/0 | 0/0 | 0/0 | 0/0 | 0/0 | 0/0 |
| 3,5-dimethyl-2-thienyl-(N-3,4-dichlorophenylcarboxamide) | 0/0 | 0/0 | 0/0 | 0/0 | 0/0 | 0/0 |
| 3,5-dimethyl-2-thienyl-(N-3,5-dichlorophenylcarboxamide) | 0/0 | 0/0 | 0/0 | 0/0 | 0/0 | 0/0 |
| 3,5-dimethyl-2-thienyl-(N-cyclohexylcarboxamide) | 0/0 | 0/0 | 0/0 | 0/0 | 20/0 | 20/0 |
| 3,5-dimethyl-2-thienyl-(N-p-tolylcarboxamide) | 0/0 | 0/0 | 0/0 | 10/0 | 10/0 | 10/0 |
| 3,5-dimethyl-2-thienyl-(N-methylcarboxamide) | 0/0 | 0/0 | 0/0 | 0/0 | 0/0 | 0/0 |

What is claimed is:

1. A compound of the formula

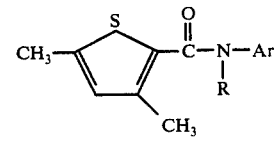

wherein R is hydrogen and Ar is phenyl or 2-fluorophenyl.

2. The compound of claim 1 wherein Ar is phenyl.

3. The compound of claim 1 wherein Ar is 2-fluorophenyl.

4. An herbicidal composition comprising a biologically inert carrier and an herbicidally effective amount of the compound of claim 1.

5. The composition of claim 4 wherein Ar is phenyl.

6. The composition of claim 4 wherein Ar is 2-fluorophenyl.

7. A method for controlling undesirable vegetation which comprises applying an herbicidally effective amount of the compound of claim 1 to the vegetation or growth medium of the vegetation.

8. The method of claim 7 wherein Ar is phenyl.

9. The method of claim 7 wherein Ar is 2-fluorophenyl.

* * * * *